US010561572B2

(12) United States Patent
Fima

(10) Patent No.: US 10,561,572 B2
(45) **Date of Patent: *Feb. 18, 2020**

(54) RECIPROCATING STIMULATION DEVICE

(71) Applicant: Alexander Fima, Austin, TX (US)

(72) Inventor: Alexander Fima, Austin, TX (US)

(*) Notice: Subject to any disclaimer, the term of this patent is extended or adjusted under 35 U.S.C. 154(b) by 0 days.

This patent is subject to a terminal disclaimer.

(21) Appl. No.: 15/664,016

(22) Filed: Jul. 31, 2017

(65) Prior Publication Data

US 2017/0326022 A1 Nov. 16, 2017

Related U.S. Application Data

(63) Continuation of application No. 14/730,329, filed on Jun. 4, 2015, now Pat. No. 9,717,645.

(51) Int. Cl.

*A61F 5/00* (2006.01)
*A61H 19/00* (2006.01)

(52) U.S. Cl.

CPC ............. *A61H 19/44* (2013.01); *A61H 19/32* (2013.01); *A61H 2201/123* (2013.01); *A61H 2201/14* (2013.01); *A61H 2201/1669* (2013.01); *A61H 2201/5007* (2013.01); *A61H 2201/5035* (2013.01); *A61H 2201/5064* (2013.01); *A61H 2201/5079* (2013.01)

(58) Field of Classification Search

CPC ......... A61H 19/00; A61H 19/40; A61H 19/44
USPC ..................................................... 600/38–41
See application file for complete search history.

(56) References Cited

U.S. PATENT DOCUMENTS 4,031,765 A * 6/1977 Metz ..................... F16H 25/122 74/57
9,717,645 B2 * 8/2017 Fima ..................... A61H 19/44
2004/0194697 A1 * 10/2004 Davis ................. B05B 13/0636 118/317
2013/0281776 A1 * 10/2013 Levy ..................... A61H 23/02 600/38

FOREIGN PATENT DOCUMENTS

WO WO2012/152297 A1 * 11/2012

* cited by examiner

*Primary Examiner* — John P Lacyk

(57) ABSTRACT

A mechanized sexual stimulation device is provided that provides a reciprocating stimulation body, preferably emulating a male in function with various length of penetration possible. Designs herein allow the protruding dildo to move back and forth to a variety of length, speeds and angles while flexing in many directions. The device includes a housing with a ball reverse screw rotatably mounted to the housing, and a reversing nut which retains bearing balls that allow the nut to move linearly up and down the ball reverse screw as the screw is turned in a single direction, thereby moving a reciprocating stimulation body such as a dildo connected (indirectly or directly) to the reversing nut. Channel or groove structures on the ball reverse screw and reversing nut guide the reciprocating back and forth stoke in a linear motion.

19 Claims, 10 Drawing Sheets

RECIPROCATING STIMULATION DEVICE

CROSS-REFERENCE TO RELATED APPLICATIONS

This application is a continuation of U.S. patent application Ser. No. 14/730,329, filed 4 Jun. 2015, and entitled "Reciprocating Stimulation Device." The entire contents of this parent application are hereby incorporated by reference.

TECHNICAL FIELD OF THE INVENTION

The invention relates to reciprocating sexual stimulation devices and drive mechanisms with internal movement therefore.

BACKGROUND OF THE INVENTION

In the sex toy industry and generally in the field of sexual stimulation devices, reciprocating type devices are known. These sexual aids are design to improve the sexual experience for one or more participants and are known in the art. Such aids vary widely in the sex toy industry. Some other known devices use a cam turned by a motor to act on a reciprocating piece. Other devices use a push rod mounted to a disc or wheel driven to push and pull the rod generally along the reciprocating direction. Generally, the latter type device has the disadvantages that it is large and uses excessive amount of battery power to drive it to be of any benefit for the user. The cam type devices suffer from limited stroke length, an awkward shape to accommodate the rotating cam, a weak drive force in the portable versions, and an asymmetry in the ascending and descending stroke force.

Another type of device is described in U.S. Pat. No. 8,308,631 to Kobashikawa et al., which uses linear movement along a screw, and reverses the motor to reverse directions. While the present inventor is not aware if such a device is commercially available, the design as presented in the therein would suffer from speed, torque and control problems and limited battery power due to the in-efficiency of the drive mechanism, and would not generally have good life of the components due the constant need for lubrication along the screw. What is needed are reciprocating stimulation devices that offer improved stroke length, while allowing portability, battery power, and drive efficiency, and ability to drive various shapes and size of reciprocating stimulation bodies for use in various toys.

SUMMARY OF THE INVENTION

Provided is a mechanized sexual stimulation device providing reciprocating or penetrating motion using an engineered ball reverser screw. The device includes a housing with a means for providing torque, such as an external torque drive attachment, or an internal motor connected by its drive shaft to a ball reverser screw. The ball reverse screw has a traveling nut which retains bearing balls that allow the nut to move linearly up and down the screw as the ball reverser screw is turned in a single direction by the motor, thereby moving a reciprocating stimulation body such as a dildo connected indirectly or directly.

While a preferred version is phallic-shaped device, other embodiments are linear reciprocating sex toys with movement using a ball screw reverser mechanism, whether male (phallic/dildo) or female (channel) shaped. In different versions, the housing may include an integrated motor coupled to the ball reverse screw through external planetary gears, a belt drive, or other torque drive. In operation, the ball reverse screw may be coupled directly or with a gear drive, or instead may employ a collar or other mount. The ball reverse screw converts rotary drive to linear reciprocating motion to be achieved by rotating the screw in one direction only. That is, the drive or motor turns in the same direction while driving the nut up and down the crew, the length of the ball reverser screw shaft dictates the device stroke length. The shaft length may vary in other models of the device. The energy of the motor dictates the speed of each back and forth stroke, converting rotary motion to reciprocating strokes. Described in as strokes per minute, the preferred embodiment of the device operates at up to 120 strokes per minute, as controlled by the user though input controls. The ball screw reverser mechanism generally includes the screw itself and a traveling nut to carry the reciprocating body. Within the travelling nut there may be various bearing balls and retainer springs.

The ball reverse screw has a shaped channel or groove acting as the inner race, with a 'reverse double helix' appearance caused by the ascending and descending helical grooves, which connect at the end of the screw at a turn-around end point. The nut has internal grooves that act as the outer race. Screw rotation causes the balls to dynamically change location within the race, or internal grooves of the travelling nut, allowing the nut to reverse from ascending to descending, and vice versa without a change of motor direction.

Unless the context dictates the contrary, all ranges set forth herein should be interpreted as being inclusive of their endpoints and open-ended ranges should be interpreted to include only commercially practical values, which may change over time according to the principles herein, such as development of new suitable materials or more powerful motors or power sources with smaller sizes. Different features may be included in different versions of the invention. These and other advantages and features of the invention will be apparent from the following description of the preferred embodiments, considered along with the accompanying drawings.

DETAILED DESCRIPTION OF PREFERRED EMBODIMENTS

Figure 1B:
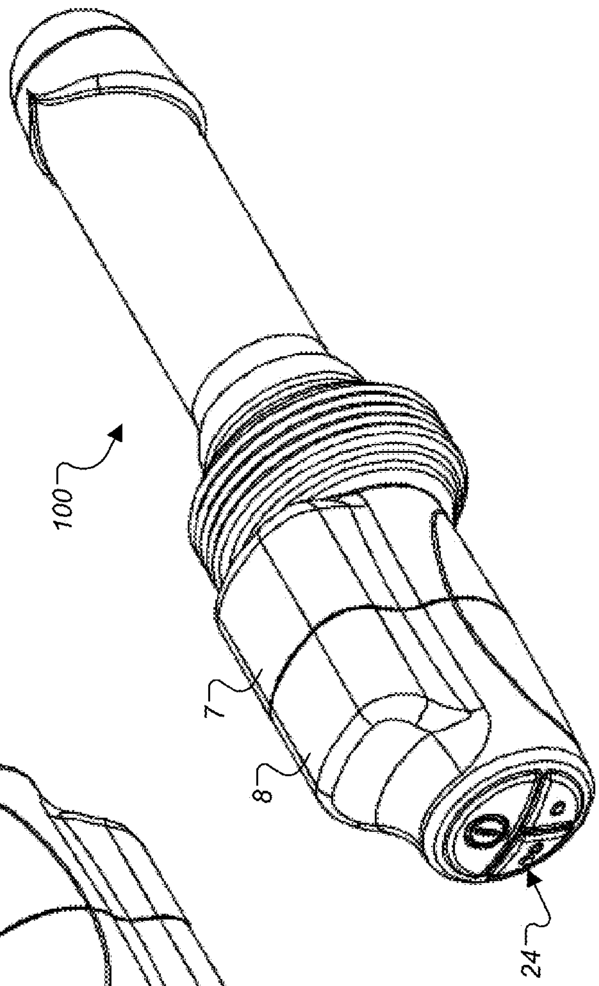
FIG. 1B is a rear perspective view of the device of FIG. 1A.
Figure 1A:
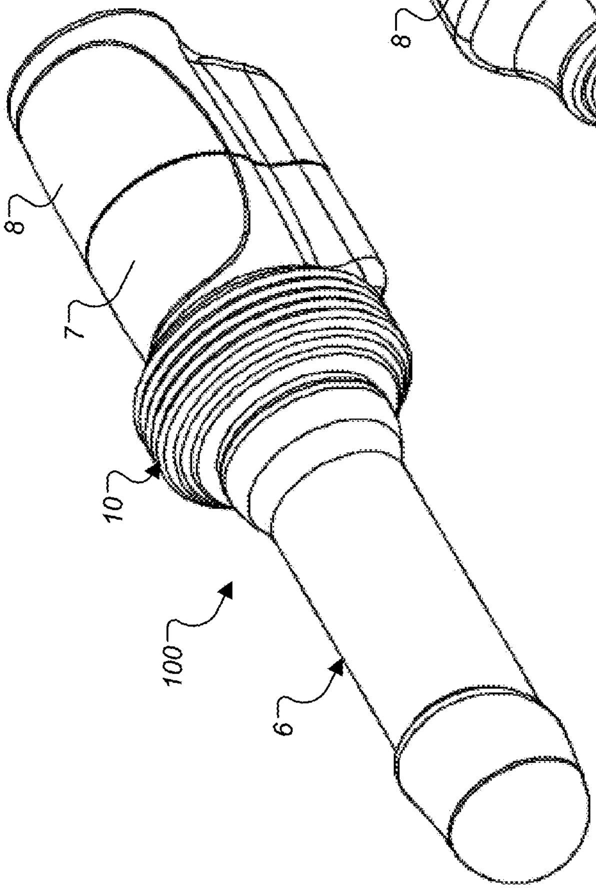
FIG. 1A is a front perspective view of a device according to one embodiment.

Provided is a mechanized sexual stimulation device 100 which provides a reciprocating action. Referring to all of the drawings, the device 100 generally includes a housing 7 and 8, a ball reverse screw 1 rotatably mounted to the housing, and a reversing nut 2 which retains bearing balls 13 that allow reversing nut 2 to move linearly up and down ball reverse screw 1 as the screw is turned in a single direction, thereby moving a reciprocating stimulation body 6 such as a dildo body 6 in this version connected (indirectly or directly) to reversing nut. FIG. 1A is a front perspective view of a device according to one embodiment. FIG. 1B is a rear perspective view of the same embodiment in a closed collapsed position. Preferably, reciprocating stimulation body 6 is a silicone or soft rubber dildo, and bellows 10 is a silicone or soft rubber bellows depicted here in a collapsed or retracted position, that protects the ball reverser screw from foreign contaminants while providing safe operation from ball reverser screw when fully extended. The bellows 10 ideally is molded as a single component with the stimulation body 6, this is intended to improve the water resistant nature of the device. While an example phallic-shaped device 100 is shown in FIGS. 1-5, this is not limiting and other embodiments may include reciprocating sex toys with movement using a ball screw reverser mechanism, whether male (phallic/dildo) or female (channel) shaped such as the reciprocating channel devices shown in FIGS. 6-7.

In the version of FIGS. 1-5, the device includes motor 16, which is a gear motor with integrated gears translating the motor rotation to apply proper torque to ball reverse screw 1. In different versions, the housing may include a suitable integrated motor coupled to the ball reverse screw directly or with a gear drive, or instead may employ a collar, shaft, hex slot or other suitable mount to attach an external drill or other torque drive.

In operation the ball screw reverser in this embodiment enables the linear reciprocating motion to be achieved by rotating the screw in one direction only. That is, the drive or motor turns in the same direction while driving traveling nut 2 is driven up and down the ball reverse screw 1 (converting torque to thrust) through screw lever forces applied by grooves 21 and 22 of ball reverse screw 1. The ball screw reverser mechanism generally includes the ball reverse screw 1 itself, the traveling nut 2, and the bearing balls 13 that operate similarly to ball bearing components, reducing friction from the movement. Ball reverse screw 1 has on its exterior a shaped groove 21, 22 acting as the inner race for the rolling bearing balls, with a ‘reverse double helix’ appearance caused by the ascending helical groove 21 and descending helical groove 22, which connect toward the proximal and distal ends of the screw at groove turnaround portions 23. Traveling nut 2 has one or more internal grooves 25 that act as the outer race or ball cage. Grooves 25 may be formed along the inner surface of traveling nut 2, or may be formed as slots passing through the structure of traveling nut 2. Ball retention spring(s) 14 encircle the nut to help contain bearing balls 15 and form, in various configurations, cages or outer races as further described below.

Figure 2:
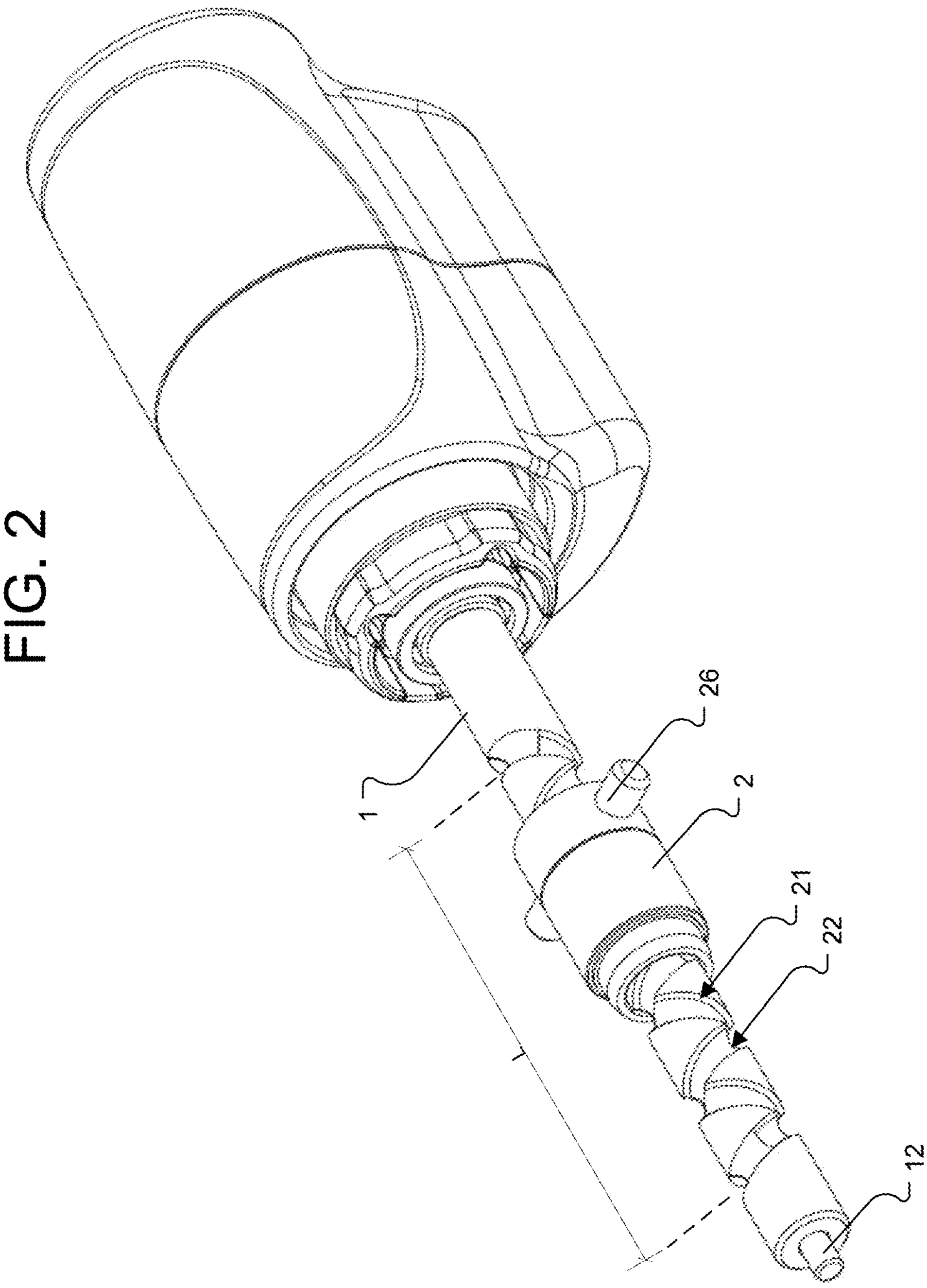
FIG. 2 is a front perspective cutaway view, showing the ball reverser screw and nut which travels thereon. Ball bearings are contained within the nut.

FIG. 2 is a front perspective cutaway view of device 100, showing the ball reverse screw 1 and traveling nut 2 which travels longitudinally thereon in a reciprocating motion, carrying the various reciprocating parts with it as driven by the ball reverse screw 1. As can be understood, the stroke length L shown measured from center to center of the turnaround portions 23 of the helical groove defines the length of travel of traveling nut 2 and the stroke length of movement of the stimulation body 6. Ball reverse screw mechanisms as described herein enable an improved stroke length L of the device without sacrificing speed, strength, or stability, as compared to prior devices that employ cams, wheels and push rods, for example. The stroke movement, in this embodiment, moves reciprocating stimulation body 6 which is connected or mounted to traveling nut 2 through two mounts 26. While ball screw driven with a single direction of rotation is preferred, this is not limiting and other versions may include a motor that is reversed, or may include a reversing mechanism for the screw other than the ascending and descending grooves as described. Front housing 7 anchors the ball bearing 11 (FIGS. 3A, 4A) to provide a raceway for the ball reverser screw 1 to rotate.

Figure 3A:
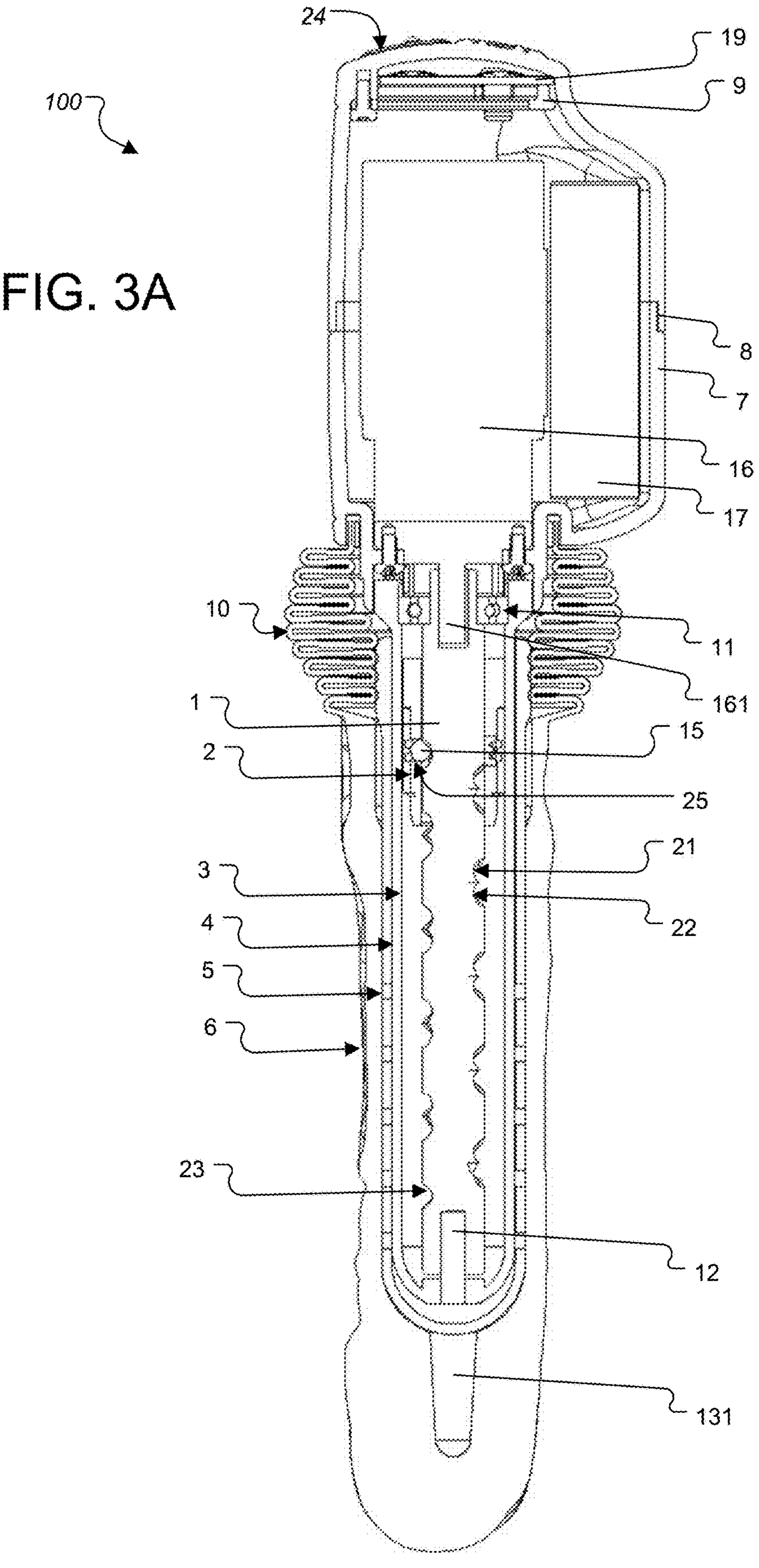
FIG. 3A is a longitudinal cross section of an example device in a collapsed position.
Figure 3B:
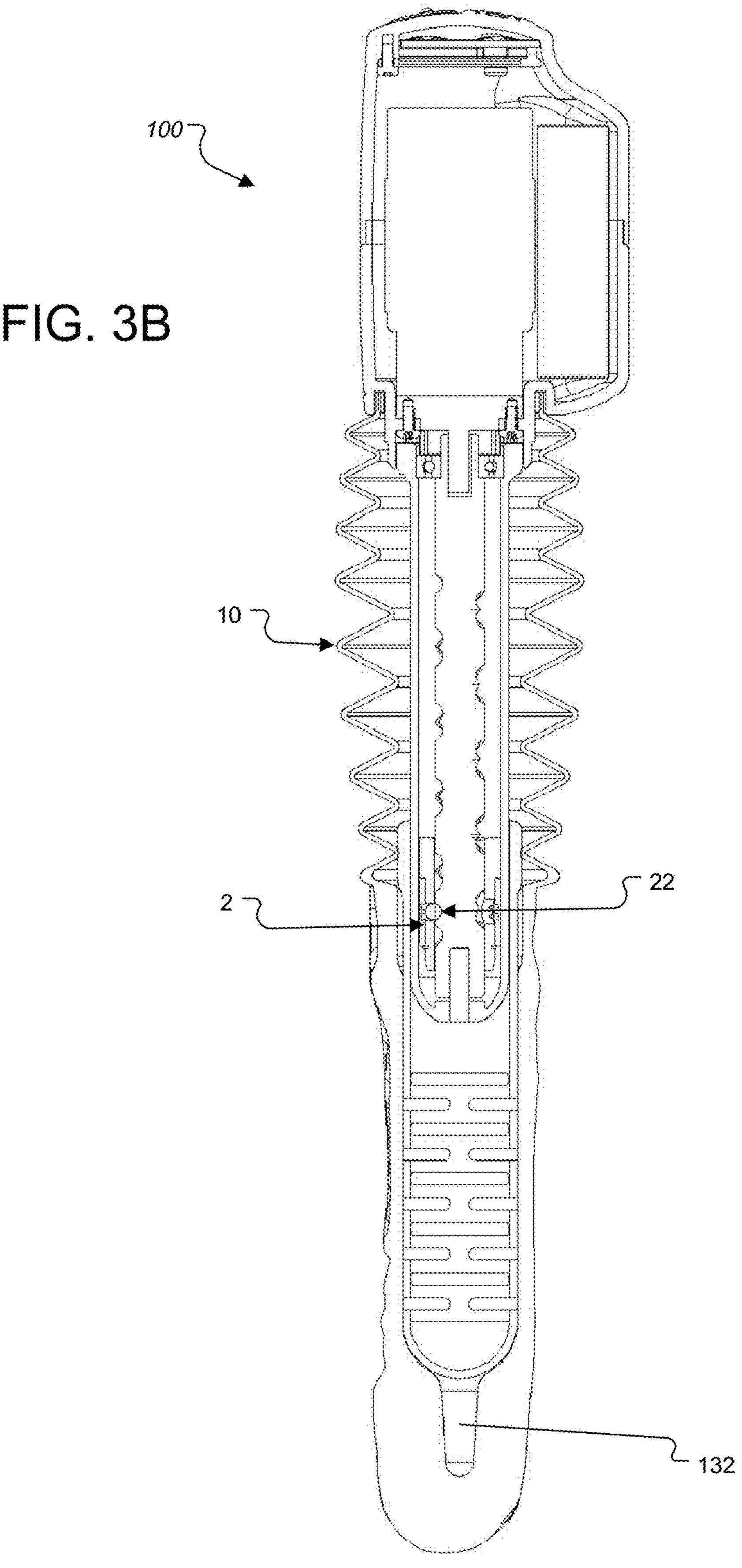
FIG. 3B is a longitudinal cross section of the example device in a fully extended position.
Figure 4A:
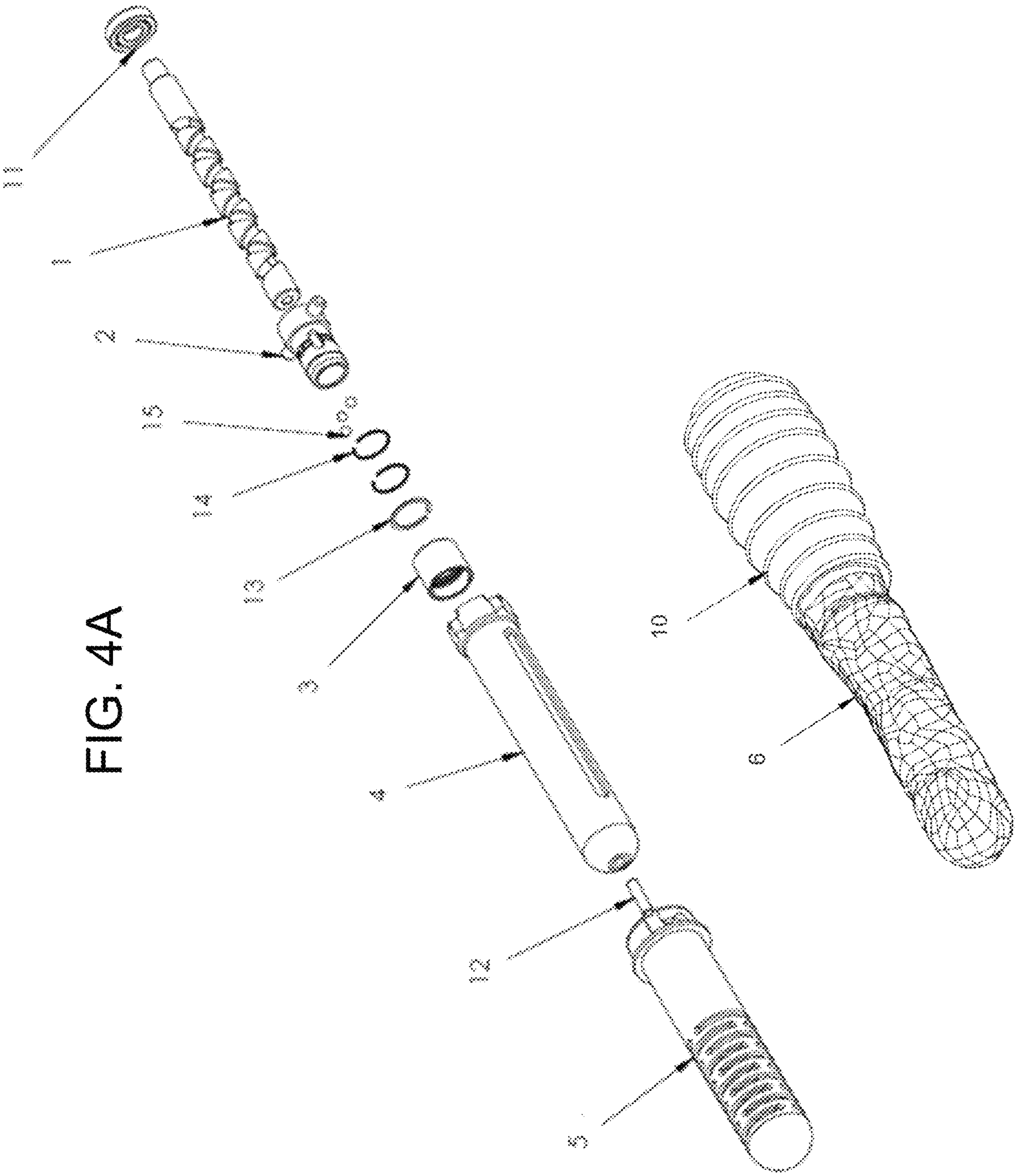
FIG. 4A is an exploded perspective view of the ball reverse screw and the components mounted thereon.
Figure 4B:
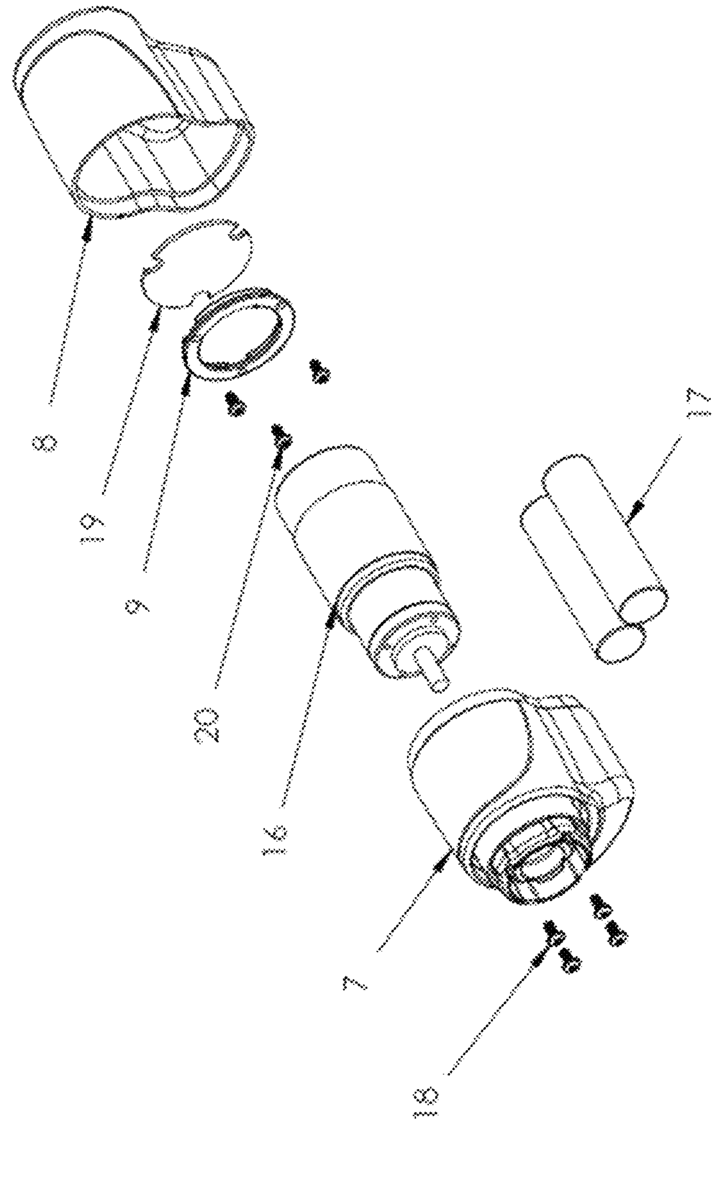
FIG. 4B is an exploded perspective view of the housing and motor assembly.

The construction and operation of this example device 100 can be further understood with reference to the FIGS. 3A-B, 4A-B, and 5. FIG. 3A shows a longitudinal cross section of the same example device 100, taken down the center of the center of the device, with the device in the retracted position, while FIG. 3B shows a similar cross section with the device in an extended position, the travelling nut 2 being shown carried to the distal end of ball reverse screw 1, with a bearing ball being depicted moved into a descending position in descending groove 22, to begin the return back down the ball reverse screw as will be discussed further below. A void 131 may be included in the stimulation body 6 to allow flexibility for flexing in many directions, and allows a rigid reinforcement structure such as a pin or spacer to be inserted to achieve a desired rigidity at the end of the range of flexure. As depicted in FIG. 3B, the silicon spacer 132 is positioned in void 131, and disconnected from the outer sleeve 5 to allow for relative such movement. FIGS. 4A and 4B show an exploded view of the same device 100, allowing one of ordinary skill in the art to understand how to construct this embodiment of the invention. FIG. 4A is an exploded perspective view of the ball reverse screw and the components mounted thereon while FIG. 4B is an exploded perspective view of the housing and motor assembly, and the bellows 10 that flexibly connects the fixed and reciprocating components to seal the interior.

Generally shown in FIG. 4B are the fixed components (meaning not reciprocating, as the screw and motor shaft and rotor will rotate) including the base assembly comprising the front and rear motor housing 6 and 7, holding gear motor 16 and its battery 17, the sealed bearing 11, the ball reverse screw 2 connected to the motor shaft, and the inner sleeve 4 mounted to the base assembly, and the dowel pin 12 mounted inside the distal end of inner sleeve 4 to rest inside a recess at the distal end of ball reverse screw 2, stabilizing inner sleeve 4 with respect to the screw. The device user controls are preferably presented along the proximal end of the device, as shown at button panel 24, which in this version includes control surfaces or buttons formed in a flexible sealed cover, allowing pressure to be placed on switches mounted to printed circuit board or control module 19.

Generally shown in FIG. 4A are the rotating ball reverse screw 1 and the reciprocating parts, which move longitudinally up and down ball reverse screw 1. These are the traveling nut 2 with its various depicted components 3, 13, 14, 15, and 26; the outer sleeve 5, and the reciprocating stimulation body 6 formed integrally with bellows 10. Outer sleeve 5 is mounted to mounts 26 of travelling nut 2, and so moves with the nut while mounts 26, which passes through the depicted slots of inner sleeve 4 to allow the mounts to reciprocate. With inner sleeve 5 being fixed, mounts 26 also prevent rotation of travelling nut 2 because they are stopped from rotation by the sides of the depicted inner sleeve slots. The outer sleeve 5 is preferably formed of a strong, rigid plastic or other suitable rigid material, serves as a relatively more rigid mount for the reciprocating stimulation body 6, which in this depicted version is a softer dildo-shaped sleeve but may have many other shapes, and may be formed of silicone or other suitable material used for the exterior of sex toys or stimulation devices. Hypo-allergenic materials may be used. Preferably, glass filled or bearing grade plastic materials are used for parts ball reverser screw and retainer nut, and plastic, metal, other materials, may be used for the other parts. Travelling nut 2 is constructed by machining, 3D printing, or molded plastic, and the ball reverse screw 1 is preferably made by injection molding but may also be made by suitable advanced 3D printing techniques or machining. This is not limiting and other versions may have the ball reverse screw 1 and travelling nut 2 formed of metal or other suitable material such as composites or carbon-reinforced material including graphene reinforced polymers.

Outer sleeve 5 may be constructed to allow for interchangeable stimulation bodies 6 of various designs, by having a cylindrical outer surface as depicted, upon which suitable stimulation bodies may be slid.

Figure 5:
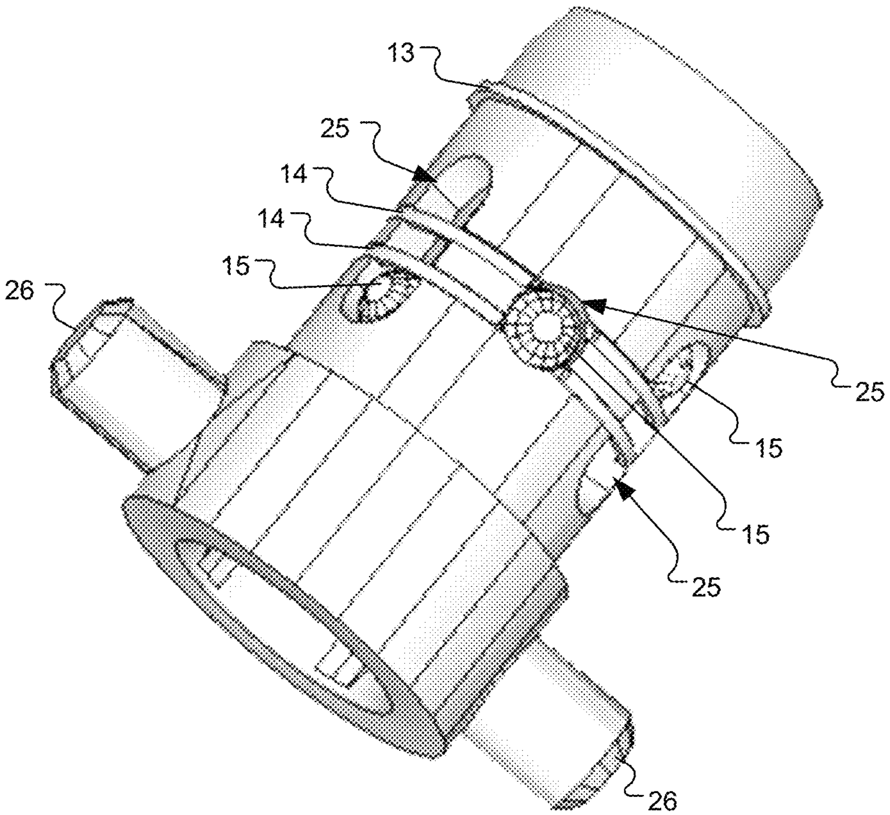
FIG. 5 is a side perspective view of a reversing nut according to some embodiments.

A preferred version of traveling nut or reversing nut 2 is shown in FIG. 5, which depicts three grooves 25 as slots formed though the body of nut 2. This is not limiting and other embodiments of the invention may employ other forms of grooves 25 or other suitable outer races to guide the bearing balls 15. As depicted, this version bearing balls 15 are held in the depicted grooves 25 such that they extend past the inner surface of traveling nut 2, allowing the balls to roll in ascending and descending grooves 21 and 22. In this embodiment, two of the grooves 25 are designed as slots with ball retention springs 14 positioned in their mounting grooves such that springs 14 pass through the outer portion of grooves 25 and act to retain bearing balls 15. Further in this version, ball retention springs 14 allow bearing balls to change from a first ascending configuration to a second descending configuration at the distal end of the ball reverse screw 1, and change from the descending configuration back to the ascending configuration at the proximal end. Such configuration change occurs in this version by movement of the two right and left depicted bearing balls in their elongated slots, by which they snap past, or force their way past, ball retention springs to occupy a new position when traveling nut 2 transitions from moving along ascending groove 21 to groove turnaround portion 23, and move again when traveling nut, or more specifically the location of the individual respective groove 25 transitions to be over descending groove 22 from the turnaround portion. A similar snap or forcing of bearing balls 15 past ball retention springs 14 occurs at a turnaround portion at the proximal end of ball reverse screw 1 as well, to allow traveling nut 2 to change configuration to reverse linear direction from descending to ascending, while ball reverse screw 1 continues rotation in a constant direction. The center depicted groove 25 allows the respective bearing ball 15 therein to rotate or roll in place rather than moving relative to the nut during the configuration change, and in this embodiment as depicted ball retention springs 14 do not impinge on the center bearing ball 15 or pass over the center groove 25.

Snap ring 13 is positioned in its mounting groove on travelling nut 2, and acts to hold reverser sleeve 3 in place over grooves 25, ball retention springs 14, and bearing balls 15. Reverser sleeve 3 acts to hold the depicted elements of traveling nut 2 in place while limiting movement of ball retention springs 14 to that required to allow bearing balls 15 to snap or force their way past springs 15 when changing configurations. When sitting in a single configuration, ball retention springs apply enough longitudinal force against bearing balls 15 to them in place as reverser screw drives them. For example, in the ascending configuration the proximal bearing ball 15 is positioned at the proximal end of its respective groove 25, and is pushed by ascending groove 21 to roll in the upward, distal direction, rotating at the ball's distal side against the proximal ball retention spring 14. At the same time, in the ascending configuration, the distal bearing ball 15 (in FIG. 5 the right-hand depicted bearing ball) is pushed by ascending groove 21 against the distal end of its respective groove 25. As traveling nut 2 transitions from the ascending configuration to the descending configuration, these ball positions are reversed and the direction of force applied by the screw is reversed, the descending force being applied by the descending groove 22. As the configuration is changed, the right and left depicted bearing balls 25 will for a brief time be in the center position of their grooves 25, between the two ball retention springs 14. Depending on the helical groove steepness and screw design, the two bearing balls may or may not occupy such center position simultaneously, with the distal ball moving through such position first when transitioning from ascending to descending configuration, and the proximal ball (the same or lead ball, now moved to the proximal position) moving through the center transition position first as the configuration is changed from descending to ascending. It may be understood that if the design is varied to include more grooves 25 on the nut, the slots may be progressively longer to allow for further movement of balls to achieve a match to the angles of the ascending and descending grooves.

While the depicted traveling nut 2 is the presently preferred embodiment, other designs are possible within the scope of the invention. For example, while three bearing balls 15 are used, other versions may use less or more, and another similar design may have two bearing balls that snap past only one ball retention spring to change the configuration from ascending to descending and back. Other versions of traveling nut 2 may use other groove or passage designs for bearing balls 15 that allow balls 15 to re-circulate or reposition in the grooves between the screw and nut, with a ball return that carries the balls from the end of their path back to the beginning to complete their circuit. More or less ball retention springs may be used. Further while one continuous helical groove is employed in this version connecting ascending and descending grooves 21 and 22 at upper and lower turnaround portions 23, other versions may employ a longer traveling nut having more than one set inner grooves acting as inner races, which may roll in more than one set of outer grooves on the ball reverse screw. For example, a long nut with a shorter stroke length, that does not traverse the entire ball reverse screw, may have a first proximal helical groove with a turnaround point less than halfway along the screw, and a second distal helical groove, separate from the proximal groove, of identical length allowing the nut to be supported and driven by bearing balls at the nuts proximal and distal halves. Other versions may provide a long nut that has bearing balls that roll in place in the nut, and travel over an un-grooved portion of the ball reverse screw. Still other versions may use other structures than bearing balls move the traveling nut along the screw. For example, other force receiving structures may be used in place of the bearing balls to receive the force from the grooves of ball reverse screw 1 and translate it to reciprocating force. In one version, at least two rounded posts, coated or constructed with Teflon or a suitable low friction material, may be employed which change configuration in races of the travelling nut similarly to the depicted balls, but do not roll. In such version, the outer race grooves of the reversing nut are configured to direct the at least two longitudinal force receiving structures to a first ascending configuration and a second descending configuration in cooperation with the ball reverse screw grooves.

Figure 6A:
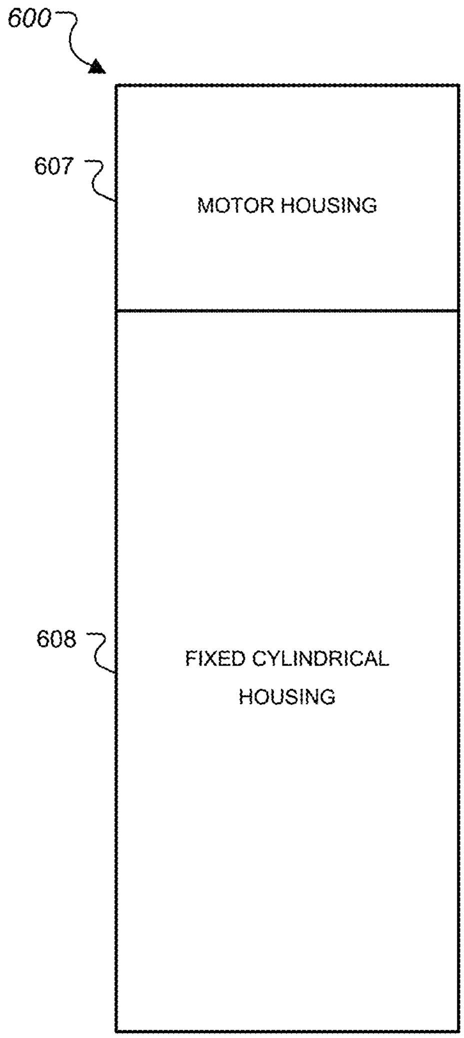
FIGS. 6A-C show schematic diagrams of a device according to another example embodiment in which a sheath or channel is reciprocated by a ball reverse cylinder.
Figure 6B:
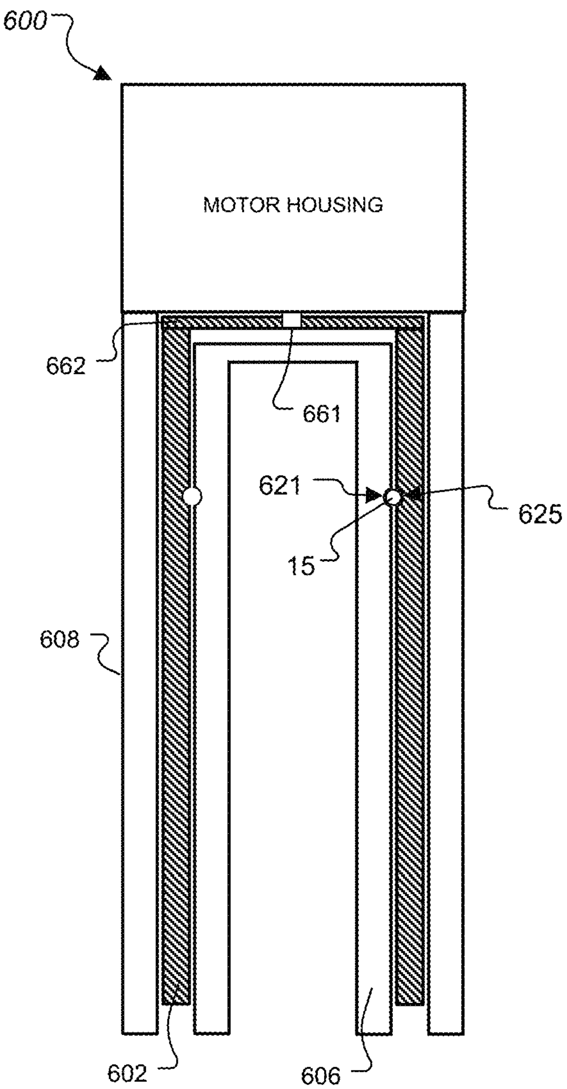
Figure 6C:
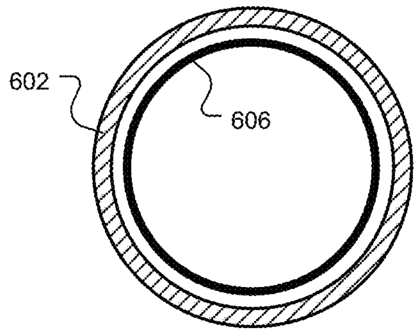

FIGS. 6A-C show schematic level diagrams of a reciprocating device 600 according to another embodiment with a reciprocating channel 606. In this version, the reciprocating stimulation body is a channel shaped body 606, providing a female type sex toy. As shown in the cutaway schematic view of FIG. 6B, rather than a ball reverse screw, the ball reverse drive mechanism in this version includes a drive cylinder 602, with interior grooves or races 625. Drive cylinder 602 is mounted to motor shaft 661 at its proximal end by mounting plate or face 662, and is rotated by the drive shaft. Inside drive cylinder 602 is the reciprocating channel 606, which is driven in longitudinal reciprocating motion along the interior helical channels or races 621 as bearing balls 15 roll or rotate in interior races 625 presented along the interior surface of drive cylinder 602. Generally, a helical race is needed to allow longitudinal movement, and the helical race may be present along the outer surface of reciprocating channel 606 or the inner surface of drive cylinder 602. The opposing surface is provided with a race 621 or 625 that allows for more limited movement of the rotating bearing balls, and may provide for change in configurations between ascending and descending configurations as is described with regard to the ball reverse screw embodiment above. Typically for a cylindrical type embodiment, more bearing balls 15 are required to stabilize the reciprocating channel 606 against the drive cylinder 602 to prevent wobbling movement.

Figure 7:
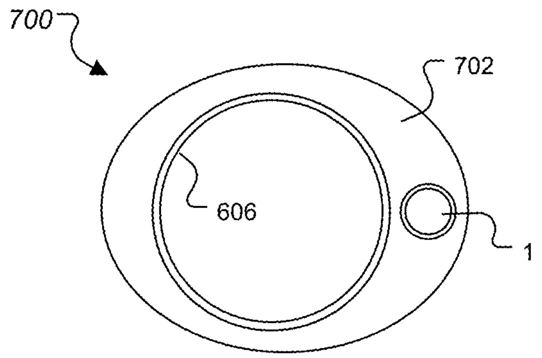
FIG. 7 is a schematic diagram of yet another example embodiment in which a sheath or channel is driven by a ball reverse screw.

FIG. 7 is a cross-section schematic view of another embodiment, showing a device 700 in which a channel 606 is driven by a ball reverse screw 1. In this version, the rotating shaft of screw 1 is positioned outside of the reciprocating channel 606, which is carried in reciprocating motion by a travelling housing 702. Travelling housing 702 includes a longitudinal channel in which ball reverse screw 1 turns, the channel provided with interior grooves or races constructed similarly to those described above with respect to travelling nut 2. In this version, the reciprocating stimulation channel may stabilized by pins that slide in one or more grooves, said one or more grooves mounted in the travelling housing distal to the reversing nut.

Figure 8:
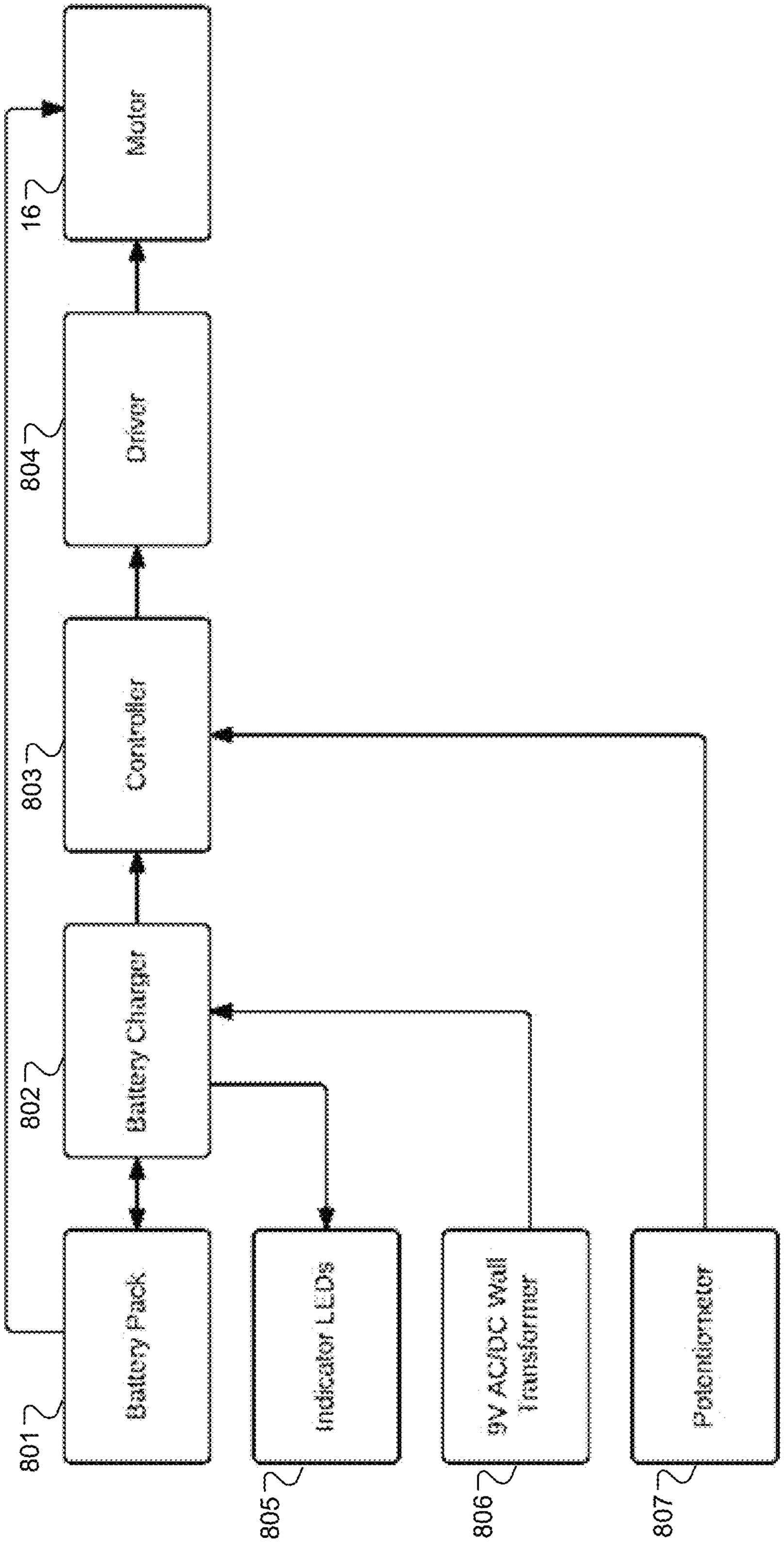
FIG. 8 is a block diagram of an example embodiment of the electrical components.

FIG. 8 is an example block diagram of electrical components for implementing the power and control features according to some embodiments. The diagram shows elements of the device control circuit, typically implemented on the printed circuit board 19, and the associated components of the device electrical system, the battery pack 801 and motor 16, and transformer 806. Generally a controller 803 mounted to PCB 19 controls the device functions, and receives user input through the buttons 24, which in this version are a power button and two fast/slow controls which adjust a potentiometer 807. Other designs may include the controller reading digital button inputs. Based on the speed setting provided from the user, the controller instructs the motor driver 804 to output an appropriate motor drive signal.

It is noted that the features herein enable faster reciprocating movement than most existing reciprocating type stimulation devices run from battery power. The low friction of the bearing balls allows a useful operating lifetime with relatively high speeds of reciprocation, as measured in strokes per minute. For example, a preferred version may vary speed from a low speed of 20 strokes per minute or under to a high speed of about 120 strokes per minute.

The controller 803 may be a special purpose analog device or a digital controller, or a mixed signal device designed to receive a speed input and control a motor. Design of the motor drive circuit is known in the art in various forms. Generally the controller controls the motor driver circuit by means of a pulse with modulation (PWM) control signal. The motor driver circuit 804 in turn regulates the speed of the motor 16. In some motor control schemes, an oscillating PWM output signal, through a power driver circuit, may be applied directly to the motor 16. Generally the controller scheme is designed to maintain or approximately maintain a desired speed in conditions of changing load on the torque drive, in order to provide a constant reciprocating speed for the device. Indicator LEDs 805 may be mounted to PCB 19 or otherwise visible to the user to indicate power on, speed, status messages such as blinking for low battery, or operating mode if different modes are provided. An AC/DC wall transformer is provided, which may be connected to the battery charger 802 in order to charge battery pack 801. The particulars of the charging or motor control circuitry are known in the art and will not be further described. It is noted that while a single motor control is shown, different embodiments may have additional motorized features such as a vibrator motor vibrating either the reciprocating stimulation body, or a vibrating stimulation piece attached to the housing.

Further, as described herein, the various features have been provided in the context of various described embodiments, but may be used in other embodiments. The combinations of features described herein should not be interpreted to be limiting, and the features herein may be used in any working combination or sub-combination according to the invention. This description should therefore be interpreted as providing written support, under U.S. patent law and any relevant foreign patent laws, for any working combination or some sub-combination of the features herein.

The above described preferred embodiments are intended to illustrate the principles of the invention, but not to limit the scope of the invention. Various other embodiments and modifications to these preferred embodiments may be made by those skilled in the art without departing from the scope of the present invention.

Any use of ordinal terms such as "first," "second," "third," etc., to refer to an element does not by itself connote any priority, precedence, or order of one element over another, or the temporal order in which acts of a method are performed. Rather, unless specifically stated otherwise, such ordinal terms are used merely as labels to distinguish one element having a certain name from another element having a same name (but for use of the ordinal term).

The invention claimed is:

1. A sexual stimulation device including:

a housing;

a ball reverse screw rotatably mounted in the housing and having a first proximal end with a torque receiving structure for applying torque to the ball reverse screw, and a second distal end;

a reversing nut adapted to hold one or more bearing balls that roll in grooves on the screw, the reversing nut adapted to move linearly up and down the screw as the screw is turned in a single direction; and a reciprocating stimulation body carried by the movement of the reversing nut, the reversing nut and ball reverse screw adapted to drive the reciprocating stimulation body in a reciprocating stroke motion in which a portion of the reciprocating stimulation body extends longitudinally past the distal end of the ball reverse screw in the distal direction.

2. The device of claim 1, further comprising an electric motor connected to the housing and coupled to the ball reverse screw torque receiving structure.

3. The device of claim 1, further including a collar connected to the ball reverse screw for coupling an external torque drive to the ball reverse screw.

4. The device of claim 1, further including an elongated inner sleeve with one or more longitudinal guide slots, the reversing nut further including one or more projections that each slide up and down a respective guide slot during movement, preventing rotation of the reversing nut relative to the housing.

5. The device of claim 4, further including an elongated outer sleeve connected to the reversing nut projections.

6. The device of claim 5, in which the reciprocating stimulation body is mounted to the outer sleeve.

7. The device of claim 1, in which the reciprocating stimulation body is a dildo body.

8. The device of claim 1, in which the reciprocating stimulation body comprises an elongated channel having an opening at a distal end.

9. The device of claim 1, in which the housing includes a bearing mount holding an annular bearing through which the ball reverse screw is mounted in order to rotate.

10. The device of claim 1, in which the grooves in the ball reverse screw include an ascending helical groove and a descending helical groove connected toward a distal end of the ball reverse screw at a groove turnaround portion.

11. The device of claim 1, further comprising a bellows fixed to a proximal end of the reciprocating stimulation body and a distal end of the housing.

12. The device of claim 1 in which the one or more bearing balls are three bearing balls, and further comprising first, second, and third outer race grooves formed in the reversing nut respectively guiding the three bearing balls.

13. The device of claim 1, in which the reversing nut includes grooves formed along its inner surface, the grooves configured as outer races to hold the one or more bearing balls.

14. The device of claim 13, in which there are at least two bearing balls, and the grooves of the reversing nut are configured to direct the at least two bearing balls to a first ascending configuration and a second descending configuration in cooperation with the ball reverse screw grooves.

15. A sexual stimulation device including:

a housing;

a reversing nut adapted to hold one or more bearing balls rotatably mounted therein;

a ball reverse drive mechanism adapted to rotate with respect to the housing and apply longitudinal force to the reversing nut, the ball reverse drive mechanism having a proximal end, a distal end, and one or more races adapted for the one or more bearing balls such that the one or more bearing balls roll in the one or more races; and a reciprocating stimulation channel structure driven by the ball reverse drive mechanism and having an opening in its distal end, the ball reverse drive mechanism adapted to drive the reciprocating stimulation channel structure in a reciprocating stroke motion in which a portion of the reciprocating stimulation channel structure extends longitudinally past the distal end of the ball reverse drive mechanism in the distal direction.

16. The device of claim 15, in which the reciprocating stimulation channel is stabilized by pins that slide in one or more grooves, said one or more grooves mounted in the housing distal to the reversing nut.

17. A sexual stimulation device including:

a housing;

a reverse screw rotatably mounted in the housing and having a first proximal end with a torque receiving structure for applying torque to the reverse screw from a motor;

a reversing nut adapted to have one or more longitudinal force receiving structures that move in a helical groove on the screw, the reversing nut adapted to move linearly up and down the screw as the screw is turned in a single direction; and a reciprocating stimulation body surrounding the circumference of the screw and reversing nut and adapted to be carried by the movement of the reversing nut in a reciprocating stroke motion in which a portion of the reciprocating stimulation body extends longitudinally past a distal end of the reverse screw in the distal direction.

18. The device of claim 17 in which there are at least two longitudinal force receiving structures, and further comprising first and second outer race grooves formed in the reversing nut respectively guiding two longitudinal force receiving structures.

19. The device of claim 18, in which the outer race grooves of the reversing nut are configured to direct the at least two longitudinal force receiving structures to a first ascending configuration and a second descending configuration in cooperation with the ball reverse screw grooves.

* * * * *